United States Patent [19]

Wiersma

[11] Patent Number: 5,797,891
[45] Date of Patent: Aug. 25, 1998

[54] SANITARY CONTROL DEVICE

[75] Inventor: Jack G. Wiersma, Jupiter, Fla.

[73] Assignee: Nouveau Technologies, Inc., Tequesta, Fla.

[21] Appl. No.: 741,143

[22] Filed: Oct. 29, 1996

[51] Int. Cl.⁶ .............................. A61F 13/15; A61F 13/20
[52] U.S. Cl. ............................ 604/360; 4/453; 4/457
[58] Field of Search ............................ 604/358–360; 119/171–173; 4/450–453, 457

[56] References Cited

U.S. PATENT DOCUMENTS

| | | | |
|---|---|---|---|
| 4,040,956 | 8/1977 | Selwitz | 4/318 |
| 4,686,937 | 8/1987 | Rosenfeld | 119/1 |
| 4,879,376 | 11/1989 | Foresta et al. | 536/18.1 |
| 4,988,505 | 1/1991 | Watanabe et al. | 424/76.3 |
| 5,120,693 | 6/1992 | Connolly et al. | 502/64 |
| 5,290,557 | 3/1994 | Mason et al. | 424/410 |
| 5,468,492 | 11/1995 | Szaloki et al. | 424/195.1 |
| 5,639,794 | 6/1997 | Emerson et al. | 514/699 |

*Primary Examiner*—John G. Weiss
*Assistant Examiner*—Tram Anh T. Nguyen
*Attorney, Agent, or Firm*—McHale & Slavin PA

[57] ABSTRACT

A saponin for use in the reduction and/or elimination of undesirable odors by placement in diapers, women's sanitary items for their menstrual cycle, bed pans, and related incontinent problems and for situations where there is a desire to control undesirable odors associated by the emission of body fluids and solids.

5 Claims, 1 Drawing Sheet

DECOMPOSITION OF ORGANIC AGRICULTURAL WASTE AND ITS CONSEQUENCES

AEROBIC AND ANAEROBIC DECOMPOSITION

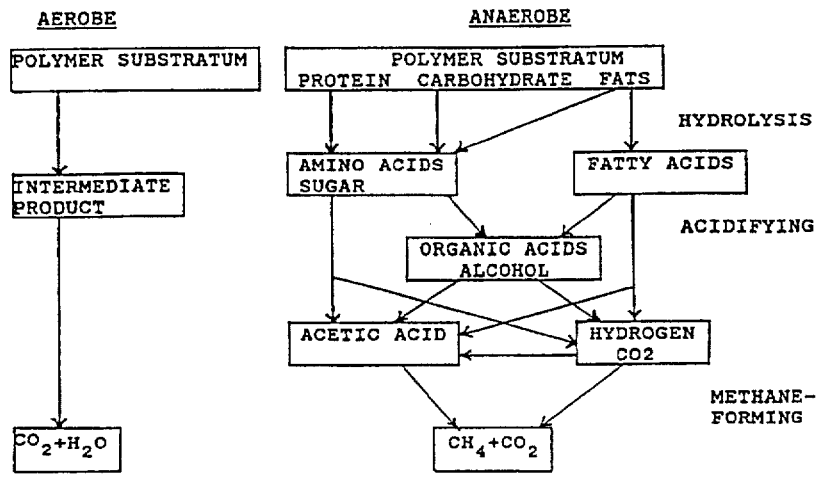

(Chemical Industries; Strategies for reduction)

NITRIFICATION $$2NH_4^+ + 3O_2 \xrightarrow{\text{NITROSOMONAS EUROPAEA}} 2NO_2 + H_2O + H^+$$

(AMMONIA) + (OXYGEN)      (NITRIT)+(WATER)+(HYDROGEN)

$$2NO_2^- + O_2 \xrightarrow{\text{NITROBACTER AGILE}} 2NO_3^-$$

(NITRITE) + (OXYGEN)      (NITRATE)

DENITRIFICATION $$2NO_3 \xrightarrow[\text{MICROCOCCUS DENITRIFICANS}]{\text{PSEUDOMONAS STUTZERI}} \text{(ANAEROBIER)} \longrightarrow N_2O$$

(NITRATE)      (DINITRIC OXIDE)

OZONE THEORY: $N_2O$ INFLUENCES THE EQUILIBRIUM OF THE GLOBAL OZONE LAYERS NEGATIVELY.

BESIDES DINITRIC OXIDE (LAUGHING GAS) NITROGEN MONOXIDE (NO) IS PRODUCED.

DECOMPOSITION OF ORGANIC AGRICULTURAL WASTE AND ITS CONSEQUENCES

AEROBIC AND ANAEROBIC DECOMPOSITION

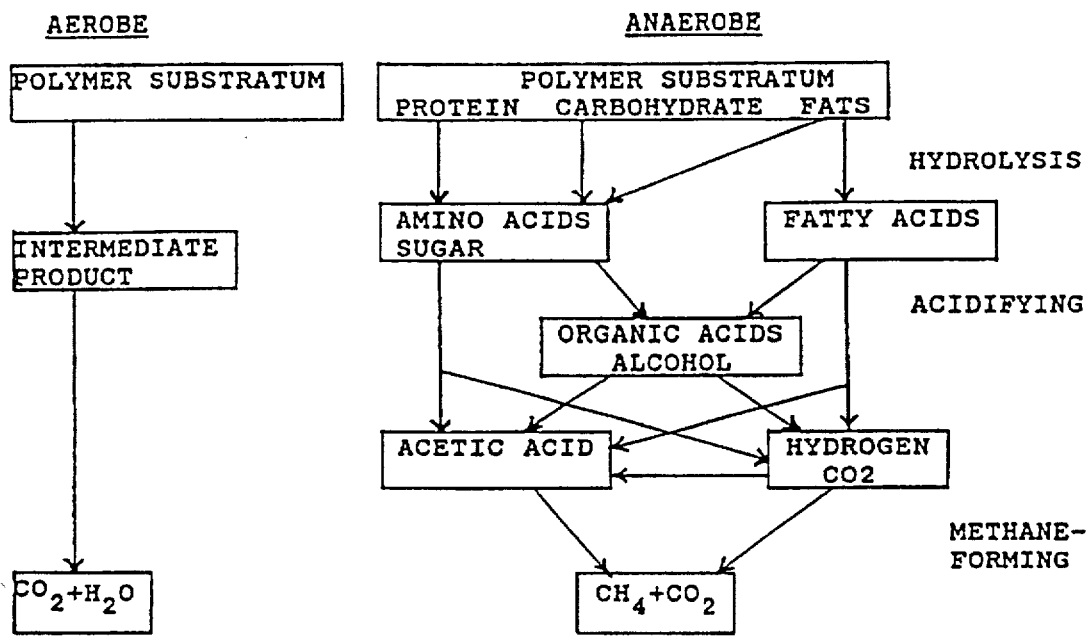

(Chemical Industries; Strategies for reduction)

NITRIFICATION

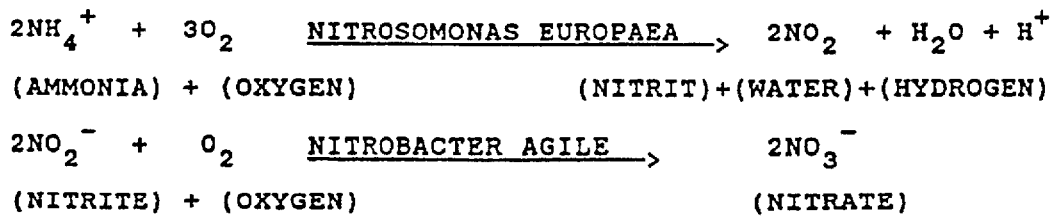

$$2NH_4^+ + 3O_2 \xrightarrow{\text{NITROSOMONAS EUROPAEA}} 2NO_2 + H_2O + H^+$$

(AMMONIA) + (OXYGEN)            (NITRIT)+(WATER)+(HYDROGEN)

$$2NO_2^- + O_2 \xrightarrow{\text{NITROBACTER AGILE}} 2NO_3^-$$

(NITRITE) + (OXYGEN)            (NITRATE)

DENITRIFICATION

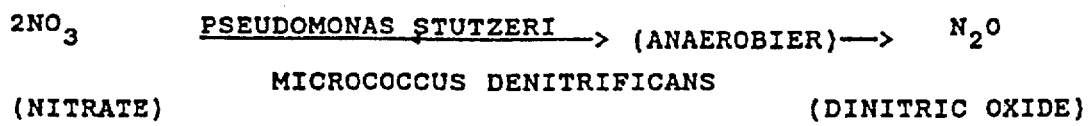

$$2NO_3 \xrightarrow[\text{MICROCOCCUS DENITRIFICANS}]{\text{PSEUDOMONAS STUTZERI}} \text{(ANAEROBIER)} \longrightarrow N_2O$$

(NITRATE)                                                           (DINITRIC OXIDE)

OZONE THEORY:   $N_2O$ INFLUENCES THE EQUILIBRIUM OF THE GLOBAL OZONE LAYERS NEGATIVELY.

BESIDES DINITRIC OXIDE (LAUGHING GAS) NITROGEN MONOXIDE (NO) IS PRODUCED.

SANITARY CONTROL DEVICE

FIELD OF THE INVENTION

This invention is related to the field of controlling undesirable body odors and in particular to the utilization of a saponin in diapers, infant and adult, women's sanitary items for their menstrual cycle, bed pads, etc., for incontinent problems and other situations for control of undesirable odors associated by the emission of body fluids and solids.

BACKGROUND OF THE INVENTION

Historically, there has been many attempts to control the uncontrolled release of noxious gases from the release of body fluids and solids from humans, both infant and adult. Even though there has been an evolution of improvement of such body fluids and solids containment, there still remains the problem of the odor generated from said body fluids and solids. The normal natural process of decomposition is accomplished by micro-organisms—primarily anaerobic. The evolving gases, especially Ammonia and Hydrogen Sulfide, are the reason for the unpleasant and often embarrassing odor. FIG. 1 demonstrates the difference between the aerobic and anaerobic process of decomposition as it relates to urine and fecal matter from animals and humans. In humans the urine represents an aqueous solution of organic and inorganic substances, the waste product of metabolism. In humans, nitrogen is excreted in the form of urea, which forms 2% of the urine on average. The feces, however, is the bodily waste material formed in the large intestine and eliminated via the anus.

According to statistics provided by MOTHERING, summer 1993, N67 P36(7) by Susan LaCroix, Sue Tibbals, Helen Moss, and Maria Fishman —GETTING TO THE BOTTOM OF THINGS. "18 billion throw-away diapers are produced annually. In the first six months a baby urinates about 20 times a day. A few minutes after the urine hits the diaper, bacteria start to grow".

It is important to note that disposable diapers are designed to contain/absorb specific amounts of urine. Example: The amount of super-absorbency polymers for infant diapers has increased in many instances from 4 to 5 grams, yielding the absorbing capacity of approximately 250 ml of urine, to 7 to 8 grams per diaper, and even 10 grams in some instances. The amount for adults fluctuates greatly from 5 to 15 grams.

The elimination of urine and feces by humans continues to create odoriferous problems both in infants and adults. This problem not only creates psychological difficulties for adults, who experience incontinence, but can be an irritant to the person themselves, as well as those around them. "Urinary incontinence has a significant impact on people over age 65. Approximately 35% of all healthy senior citizens, as well as half of all residents of long-term care, have urinary incontinence. Urinary incontinence is one of the three leading reasons for institutionalization of the elderly. With age, kidneys produce more urine at rest. Elderly people may produce ⅔ to ¾ of their total urinary output at night." (Achieving Continence, by Diane Smith/Anne Nichols, Nonwovens Industry, September, 1995.) Urinary incontinence is always life-altering, not only due to changing habits, but also from the odor associated with incontinence, leaving the affected party embarrassed because of the associated odor.

Additionally, the feminine hygiene industry has long sought a safe and economically feasible method of controlling the odors generated from a woman's menstrual cycle when contained in the various "receptor" materials designed and produced to contain the shedding of the uterine lining each month in the absence of pregnancy. One of the major obstacles has been the ability to control the undesirable odors by the inclusion of an appropriate composition in the "receptor"/absorbent materials which is safe, non-irritating and does not cause what is referred to as "toxic shock syndrome". "In 1991, worldwide consumption of sanitary napkins was approximately 43 billion units, an increase of 1.9% over 1990. The 1991 market was valued at almost $4.1 billion". (A Worldwide Overview of the Sanitary Market by Guy Goldstein, Source — Nonwovens Industry, April, 1993, V24 N4P42(6).)

Thus, what is lacking in the art is the need for a composition capable of reducing or eliminating the odors caused by bodily emissions in a safe and efficacious way.

SUMMARY OF THE INVENTION

The instant invention is a colloidal composition employing saponin that, when applied under certain conditions, is capable of reducing or eliminating the odors associated with the bodily emissions of fluids and solids when said fluids and solids are contained on or in those "Receptor" materials designed to contain said body fluids and solids. In particular, a triterpene saponin is used which is non-steroidal and commercially available. The saponin functions as a bioactivator when exposed to body fluids and solids and promotes the aerobic process vs. the anaerobic process, thereby controlling or eliminating the undesirable odors in the beginning of the decontamination process.

Triterpene saponin is slightly acidic having a pH of between 4 and 5, more close to 5, and because the molecular structure of the triterpene saponin is colloidal, it does not penetrate the body's tissue or blood stream, thereby eliminating the potential of irritation to the exposed body cavities and surrounding tissue and eliminating the potential of "toxic shock syndrome".

The composition is preferably applied by a mechanical device, calibrated, insuring that according to prescribed application rates, an evenly distributed amount of the composition covers the entire surface to be treated. With respect to this invention, the treated surface includes, but is not limited to, super-absorbent polymers, non-wovens, synthetic and natural fibers and materials.

Thus, an objective of this invention is to reduce or eliminate odors associated with bodily emissions, contained or absorbed, in or on, the "receptor" materials designed to contain or absorb such bodily emissions.

Another objective of this invention is to teach a process of controlling odors of body fluids and solids that is economical, simple to apply, safe with respect to the human body, and additionally, is environmentally friendly.

Still another objective of the instant invention is to provide a process that requires minimal mechanical adjustments to accommodate the normal production of existing processing programs associated with the manufacture and production of said "receptor" materials for the containment or absorbent properties for which they are designed.

Other objects and advantages of this invention will become apparent from the following description, wherein are set forth by way of illustration and example, certain embodiments of this invention.

BRIEF DESCRIPTION OF THE DRAWING

FIG. 1 is a chart illustrating the difference between an aerobic and anaerobic process of decomposition as it relates to urine and fecal matter from animals and humans.

DETAILED DESCRIPTION OF THE PREFERRED EMBODIMENT

Saponins are naturally occurring oily glycosides that occur in a wide variety of plants, including acacia, soapwort, soaproot, California pigweed, and many others. The use of a triterpene saponin, commonly referred to as Saponin Departum Levissium Q, is non-steroidal and commercially available. The preferred embodiment of this invention is directed to the Triterpene Saponin, yet it will be obvious to one of ordinary skill in the art that the various types of saponins, or parts and extracts thereof, may be substituted, leading to various levels of success. An artificial reproduction of saponin is deemed within the scope of this invention.

The instant invention is a colloidal composition employing a saponin capable of reducing or eliminating the associated odors of fluids and solids emitted from the body, in or on the "receptor" materials designed for absorbing or containing said fluids and solids. The utilization of triterpene saponin, having an environmentally safe, non-steroidal make up, which operates as a bio-activator, uncovered a unique property capable of reducing or eliminating the odors associated with the emitted body fluids and solids without being a masking agent or deodorant, many of which create an irritant problem when incorporated into or on the "receptor" materials previously described in this paper.

As previously mentioned, the saponin used in the creation of this composition is colloidal. The colloidals are thus intermediate between core suspensions on the one hand and molecular on the other. Because the molecular structure of the triterpene saponin is colloidal, it does not penetrate the substrate. In instances where the composition is used in the treatment of body wastes which are contained or absorbed in or on the designed "receptor" materials, the triterpene saponin penetrates only to the substrate of the material being treated. Therefore, when the composition is incorporated into the "receptor" materials it, in effect, covers the material and allows it to perform its bio-active function whether the inclusion was in a dry form or a liquid form, subsequently dried. Additionally, if the composition, through or by one form or another, comes directly into contact with any exposed body cavity, because of its molecular structure, it will not enter into the tissue or blood stream of the person(s) so exposed.

Further, as stated in the German Patent No. P 44 00 375.7-41titled "Usage of Pathogen Killing Foams",a triterpene saponin is used to protect the cavity lining of the vagina and uterus. This gives further evidence that not only is a triterpene saponin, because of its colloidal properties, safe when exposed to human and animal body cavities, but one could conclude that it also does not create the problem of "toxic shock syndrome".

It should be noted that if, or when, a deodorant, masking agent, or other forms of safe, non-irritating compositions are found to be effective, that the triterpene saponin offers a wide range of compatibility. This range is generally determined by the pH factor in the range from 4 to 10 on the pH scale. Additionally, because of the triterpene saponin's unique characteristics, it is possible, when desired, that a reduced amount of an acceptable masking agent or deodorant could be included in the process utilizing the triterpene saponin as not only an enhancement, but as a carrier, thereby reducing the needed amount of the added masking agent or deodorant.

It is contemplated that the inclusion of a triterpene saponin composition administered during the production process of the designed "receptor" materials would be of minimal consequence since the composition can be either sprayed on or in the "receptor" materials or added in a dry form at pre-measured quantities.

Further, it has been determined by recognized European and United States University studies, that when a triterpene saponin, applied at recommended rates, is topically applied to human and animal waste, a reduction of oders in order of approximately 35% to 75% occurs. Additionally, numerous field tests have demonstrated the same results both in Europe and the United States. These university students and field trials indicate the nearly complete stabilization of nitrogen along with the near elimination of sulfides. This is accomplished by the bio-active properties recognized in the literature of the saponin.

The method of inclusion of a saponin into the "receptor" material designed by industry, such as diapers, both infant and adult pads, etc., designed for incontinent people in long-term care facilities, hospitals, or in a residential environment, women's sanitary products such as what is commonly referred to as tampons, pads, panty shields, etc., is accomplished by, for example only, misting or spraying of the composition at the recommended application rate on the super-absorbent polymers prior to inclusion into the "receptor" materials, and dried or with a dry form of the saponin composition, applied to or included in the insertion of the super-absorbent polymers into the "receptor" materials. Additionally, where super-absorbent polymers are not used, the above-mentioned method can be incorporated directly into the non-woven "receptor" materials.

The recommended rate of application of the preferred embodiment is based on the pre-designed absorbent and/or containment capacity. By example, but not limited to, the amount of the preferred embodiment, a triterpene saponin previously referred to as Saponin Departum Levissium Q, for the average infant diaper would be from one to three drops or its equivalent amount in a dry form, said infant diaper designed to contain up to 250 ml of urine. This rate of application and choice of method will vary in direct proportion to the designed capacity of the "receptor" materials.

It is to be understood that while a certain form of the invention is illustrated, it is not to be limited to the specific constituents or method of application herein described and shown. It will be apparent to those skilled in the art that various changes may be made without departing from the scope of the invention.

What I claim is:

1. A sanitary control device comprising a means for receiving absorbing fluids and solids emitted from a human body, said means for receiving selected from the group consisting of diapers, women's sanitary products, and bedpans, and said means containing a superabsorbent polymer or non-woven receptor material, and a non-steroidal colloidal composition having an effective amount of dry triterpene saponin stored on said means for receiving; wherein said colloidal composition is capable of neutralizing odors from the absorbed fluids and solids.

2. The sanitary control device according to claim 1 wherein said colloidal composition has a ph range between 4 and 10.

3. The sanitary control device according to claim 1 wherein said colloidal composition is combined with a polymer formed integral to said means for receiving.

4. The sanitary control device according to claim 1 wherein said colloidal composition is incorporated into a non-woven means for receiving.

5. The sanitary control device according to claim 1 wherein said triterpene saponin is Saponin Departum Levissium Q.

* * * * *